United States Patent
Tan et al.

(10) Patent No.: US 8,791,227 B1
(45) Date of Patent: Jul. 29, 2014

(54) CROSSLINKED AROMATIC POLYIMIDES AND METHODS OF MAKING THE SAME

(75) Inventors: Loon-Seng Tan, Centerville, OH (US); David Huabin Wang, Beavercreek, OH (US); Hilmar Koerner, Beavercreek, OH (US); Richard A. Vaia, Beavercreek, OH (US)

(73) Assignee: The United States of America as represented by the Secretary of the Air Force, Washington, DC (US)

(*) Notice: Subject to any disclaimer, the term of this patent is extended or adjusted under 35 U.S.C. 154(b) by 44 days.

(21) Appl. No.: 13/546,439

(22) Filed: Jul. 11, 2012

Related U.S. Application Data

(60) Provisional application No. 61/636,134, filed on Apr. 20, 2012, provisional application No. 61/636,170, filed on Apr. 20, 2012.

(51) Int. Cl.
*C08G 69/26* (2006.01)

(52) U.S. Cl.
USPC .......................... 528/342; 528/340

(58) Field of Classification Search
USPC .................................. 528/340, 342
See application file for complete search history.

(56) References Cited

U.S. PATENT DOCUMENTS

| | | | |
|---|---|---|---|
| 3,455,879 A | 7/1969 | Gay et al. | |
| 3,835,120 A | 9/1974 | Bach et al. | |
| 4,107,125 A | 8/1978 | Lovejoy | |
| 4,271,288 A | 6/1981 | Woo | |
| RE30,922 E * | 5/1982 | Heilman et al. | 524/104 |
| 4,394,499 A | 7/1983 | Robinson et al. | |
| 4,728,697 A | 3/1988 | Bolon et al. | |
| 4,981,497 A * | 1/1991 | Hayes | 95/51 |
| 5,101,005 A * | 3/1992 | Vora et al. | 528/183 |
| 5,101,037 A | 3/1992 | McGrath et al. | |
| 5,175,234 A * | 12/1992 | Lubowitz et al. | 528/173 |
| 5,300,559 A * | 4/1994 | Sheehan et al. | 524/714 |
| 5,344,894 A * | 9/1994 | Lubowitz et al. | 525/422 |
| 5,516,876 A * | 5/1996 | Lubowitz et al. | 528/170 |
| 5,599,582 A * | 2/1997 | Adamopoulos et al. | 427/207.1 |
| 5,670,651 A * | 9/1997 | Tan et al. | 548/219 |
| 5,965,687 A * | 10/1999 | Jensen | 528/86 |
| 6,184,333 B1 * | 2/2001 | Gray | 528/170 |
| 6,262,223 B1 * | 7/2001 | Meador et al. | 528/353 |
| 6,307,008 B1 * | 10/2001 | Lee et al. | 528/353 |
| 6,509,094 B1 * | 1/2003 | Shah et al. | 428/395 |
| 7,582,722 B1 * | 9/2009 | Tan et al. | 528/423 |
| 7,678,873 B1 * | 3/2010 | Tan et al. | 528/128 |
| 8,173,763 B1 * | 5/2012 | Tan et al. | 528/223 |
| 8,389,619 B1 * | 3/2013 | Tan et al. | 524/496 |

(Continued)

FOREIGN PATENT DOCUMENTS

JP 2005154643 A * 6/2005 ............. C08G 73/10

OTHER PUBLICATIONS

Meador et al. (Polymer Preprints 2010, 51(1), 265-266).*

(Continued)

*Primary Examiner* — Liam J Heincer
(74) *Attorney, Agent, or Firm* — AFMCLO/JAZ; Rebecca Greendyke

(57) ABSTRACT

A crosslinked aromatic polyimide having shape memory properties and methods of making the same. The crosslinked aromatic polyimide comprises at least one aromatic diamine, at least one dianhydride monomer, and a tri(oxybenzene-amine) crosslinker. The crosslinked aromatic polyimide polymers and films possess superior shape memory properties at temperatures above 225° C.

16 Claims, 5 Drawing Sheets

(56) References Cited

U.S. PATENT DOCUMENTS

| | | | | |
|---|---|---|---|---|
| 2003/0064235 | A1* | 4/2003 | Okawa et al. | 428/473.5 |
| 2005/0080229 | A1* | 4/2005 | Deets et al. | 528/310 |
| 2006/0217482 | A1* | 9/2006 | Lukehart et al. | 524/495 |
| 2006/0235194 | A1* | 10/2006 | Kato | 528/353 |
| 2006/0270825 | A1* | 11/2006 | Angermeier et al. | 528/310 |
| 2007/0106056 | A1* | 5/2007 | Itatani | 528/310 |
| 2007/0270562 | A1* | 11/2007 | Yamada et al. | 528/26 |
| 2008/0025905 | A1* | 1/2008 | Wang et al. | 423/447.1 |
| 2008/0311303 | A1* | 12/2008 | Naiki et al. | 427/393.5 |
| 2009/0220722 | A1* | 9/2009 | Wang | 428/64.1 |
| 2010/0048745 | A1* | 2/2010 | Yamada et al. | 521/61 |
| 2011/0009513 | A1* | 1/2011 | Chaudhary et al. | 521/134 |
| 2011/0136061 | A1* | 6/2011 | Itatani | 430/270.1 |

OTHER PUBLICATIONS

Meador et al. (ACS Spring National Meeting 2011; Anaheim, CA; Mar. 20-26, 2011; United States).*
Machine Translation of JP 2005154643 A, 2013.*
Straub, Darel K., "Lewis Structures of Boron Compounds Involving Multiple Bonding," Journal Chem. Ed., 72(6), (1995), 494-497.
Chao, Tsung-Yi, et al., "Nonlinear optical polyimide/montmorillonite nanocomposites consisting of azobenzene dyes," Dyes and Pigments 77 (2008) 515-524.
United States Patent and Trademark Office, Non-Final Office Action in Related Case, U.S. Appl. No. 13/557,326, Mail Date Sep. 26, 2012.
United States Patent and Trademark Office, Non-Final Office Action in Related Case, U.S. Appl. No. 13/557,326, Mail Date Mar. 27, 2013
Wang, D.H., et al., "Photomechanical Response of Glassy Azobenzene Polyimide Networks," Macromolecules 2011, 44, pp. 3840-3846.
Pyun, Eomi, et al., "Kinetics and mechanisms of thermal imidization of a polyamic acid studied by ultraviolet-visible spectroscopy", Macromolecules (1989), 22(3), 1174-83.
Hosono, Nobuhiko, et al., "Photochemical control of network structure in gels and photo-induced changes in their viscoelastic properties" Colloids and Surfaces, B: Biointerfaces (2007), 56(1-2), 285-289.
Zhang, Chaohui, et al., "Rapid bending of a nonliquid crystal azobenzene polymer film and characteristics of surface relief grating" Journal of Applied Polymer Science (2009), 113(2), 1330-1334.
Hergenrother, P.M., "Recent Developments in High Temperature Organic Polymers," Polyimides and Other High-Temperature Polymers, Abadie, M.J.M. and Sillion, B., Eds., Elsevier: New York, 1991, pp. 1-18.
Agolini, F., et al., "Synthesis and Properties of Azoaromatic Polymers," Macromolecules (May-Jun. 1970), vol. 3, No. 3, 349-351.
White, T.J., et al., "A high frequency photodriven polymer oscillator," J. Soft Matter 2008,4, 1796-1798.
White, T.J., et al., "Polarization-controlled, photodriven bending in monodomain liquid crystal elastomer cantilevers," J. Mater. Chem. 2009, 19, 1080-1085.
Lee, K.M., et al., "Relationship between the Photomechanical Response and the Thermomechanical Properties of Azobenzene Liquid Crystalline Polymer Networks," Macromolecules 2010, 43, 8185-8190.
Sroog, C.E., "Polyimides," Prog. Polym. Sci. 1991, 16, 561-694.
Koshiba, Y., et al., "Photo-induced alignment behavior of azobenzene compound in thin film," Thin Solid Films 2009, 518, 805-809.
Koerner, H., et al., "Photogenerating work from polymers," Mater. Today (Oxford, U. K.) 2008, 11, (7-8), 34-42.
Wang, D.H., et al., "Nanocomposites Derived from a Low-Color Aromatic Polyimide (CP2) and Amine-Functionalized Vapor-Grown Carbon Nanofibers: In Situ Polymerization and Characterization," Macromolecules 2007, 40, 6100-6111.
Arlen, M., et al., "Thermal-Electrical Character of in Situ Synthesized Polyimide-Grafted Carbon Nanofiber Composites," Macromolecules 2008, 41, 8053-8062.
Lee, Kyung Min, and White, Timothy J., "Photomechanical Response of Composite Structures Built from Azobenzene Liquid Crystal Polymer Networks," Polymers (2011), 3, 1447-1457.
Behl, Marc, et al., "Shape-memory polymers" Materials Today (Oxford, United Kingdom) (2007), 10(4), 20-28.
Xie, Tao, "Recent advances in shape memory polymer," Polymer (2011), 52(22), 4985-5000.
Liu, C., et al., "Review of progress in shape-memory polymers," Journal of Materials Chemistry (2007), 17(16), 1543-1558.
Koerner, Koerner, et al., "Polymer design for high temperature shape memory: Low crosslink density polyimides," Polymer(2013), 54, 391-402.
Shumaker, J.A., et al, "Synthesis of high temperature polyaspartimide-urea based shape memory Polymers," Polymer (2012), 53, 4637-4642.
Jeong, K.U., et al., "Adhesion property of novel polyimides containing fluorine and phosphine oxide moieties" J. Adhesion Sci. Technol., vol. 15, No. 14, pp. 1787-1803 (2001).
Whitaker, Craig M., et al., "Synthesis and Solid-state Structure of Substituted Arylphosphine Oxides," Journal of Organic Chemistry (1995) 60, 3499-3508.
Sinou, Denis, et al., "Synthesis of a Family of Triarylphosphanes with Fluorous Phase Affinity," European J. Org. Chem. 2002, 269-275.
Schuh, Christian, et al., "Shape-Memory Properties of Segmented Polymers Containing Aramid Hard Segments and Polycaprolactone Soft Segments," Polymers 2010, 2, 71-85.
Rabani, Gouher, et al., "Synthesis and characterization of two shape-memory polymers containing short aramid hard segments and poly(3-caprolactone) soft segments," Polymer (2006) 47, 4251-4260.
Makita, Shohei, et al., "Synthesis of Alkaline-Developable, Photosensitive Hyperbranched Polyimides through the Reaction of Carboxylic Acid Dianhydrides and Trisamines," Journal of Polymer Science Part A: Polymer Chemistry, vol. 42, 3697-3707 (2004).
Lendlein Andreas et al., "Shape-Memory Polymers," Angewandte Chemie, International Edition, vol. 41, 2034-2057 (2002).
Liu C. et al, "Review of Progress in Shape-Memory Polymers," Journal of Materials Chemistry, vol. 17, 1543-1558 (2007).
Fay, Catherine C. et al., "Molecularly Oriented Polymeric Thin Films for Space Applications," High Performance Polymers, vol. 11, 145-156 (1999).
SRS Technologies and Mantech Materials, "Polyimides: CP1 and CP2 Film Properties," printed Jul. 9, 2012, 1 page, available at <http://www.mantechmaterials.com/_images/documents/3_8_doc.pdf>.
St. Clair, Anne K., et al. "Synthesis and Characterization of Essentially Colorless Polyimide Films," J. Polym. Mater. Sci Eng., vol. 51, pp. 62-66 (1984).
Miner, Gilda A., et al, "The Wettability of LaRC Colorless Polyimide Resins on Casting Surfaces," J. Polym. Mater. Sci Eng., vol. 76, pp. 381-382 (1997).
U.S. Patent and Trademark Office, Non-Final Office Action mailed Feb. 10, 2014, U.S. Appl. No. 13/866,551, 5 pages.

* cited by examiner

CROSSLINKED AROMATIC POLYIMIDES AND METHODS OF MAKING THE SAME

CROSS-REFERENCE TO RELATED APPLICATIONS

This application is related to, and claims priority from, U.S. Provisional Patent Application No. 61/636,134, filed on Apr. 20, 2012, by inventor Loon-Seng Tan, et al., and entitled "Multi(Azobenzene-Amine) Photo-Active Crosslinkers," and U.S. Provisional Patent Application No. 61/636,170, filed Apr. 20, 2012, by inventor Loon-Seng Tan, et al., and entitled "Azobenzene-Containing Glassy Polyimides Capable of Photo-Induced Large-Angle Bending," both of which are incorporated herein by reference in their entirety.

RIGHTS OF THE GOVERNMENT

The invention described herein may be manufactured and used by or for the Government of the United States for all governmental purposes without the payment of any royalty.

BACKGROUND OF THE INVENTION

1. Field of the Invention

This invention relates generally to the field of crosslinked polyimides. More particularly, it relates to crosslinked aromatic polyimides having shape memory properties at elevated temperatures and methods of making the same.

2. Description of the Related Art

Shape memory materials, including shape memory polymers (SMPs) and shape memory alloys (SMAs) are a class of active materials can be programmed to "fix" a temporary shape or a series of temporary shapes and to recover to a "memorized" permanent shape upon application of a predetermined external stimulus. The permanent shape of most SMPs is established during the manufacturing process by a network of covalent or physical crosslinking. While the shape memory effects of SMAs stem from martensitic/austenitic transitions (changes in crystal structure), the shape memory effect of thermally-induced SMPs is driven by heating the polymer above its glass transition temperature ($T_g$) or melting point ($T_m$), which causes the SMP to become soft and elastomeric in nature. The heated SMP may be deformed into one or more temporary shapes. The SMP is then cooled below the $T_g$ or $T_m$ while still under stress, causing immobilization of the constituent network chains to fix the temporary shape. Recovery of the permanent shape is then accomplished by heating the SMP above the $T_g$ or $T_m$, which remobilizes the network chains and allows rubber (entropic) elasticity to return the SMP to its equilibrium or permanent shape. Other types of SMPs include light-induced, electro-active, pH-responsive, and water/moisture-driven SMPs.

SMPs and SMAs have been widely used in actuation, robotics, and piping, as components in aircraft and automobiles, and in medical and dental applications. SMPs possess many properties that make them more attractive than SMAs, such as much lower cost, easier manufacturing and processing using conventional methods, higher capacities for elastic deformation (up to 200% in most cases), lower density, and a broader range of customizable application temperatures. In addition, many SMPs have the potential for biocompatibility and biodegradability. However, most currently available SMPs consist of high-alkyl content polymers such as polyurethane, poly(ε-caprolactone), poly(norbornene), (ethylene-oxide)/(ethylene terephthalate)-based copolymers, styrene/butadiene copolymers, thiolene/acrylate copolymers, etc. Many of these SMPs do not possess shape memory properties above 150° C., nor do they possess long-term thermal and thermo-oxidative stability in this temperature region.

SUMMARY OF THE INVENTION

The present invention includes crosslinked aromatic polyimide polymers and films having shape memory properties at elevated temperatures ranging from 228° C. to 246° C. The crosslinked aromatic polyimides comprise at least one aromatic diamine, at least one dianhydride monomer, and a tri (oxybenzene-amine) crosslinker with the following general formula, wherein W is selected from a group consisting of $CH_3C$, N, P=O, or $BO_3$; R is selected from a group consisting of H, F, Cl, $CF_3$, or $CH_3$; and the amine groups ($NH_2$) are located meta or para with respect to R:

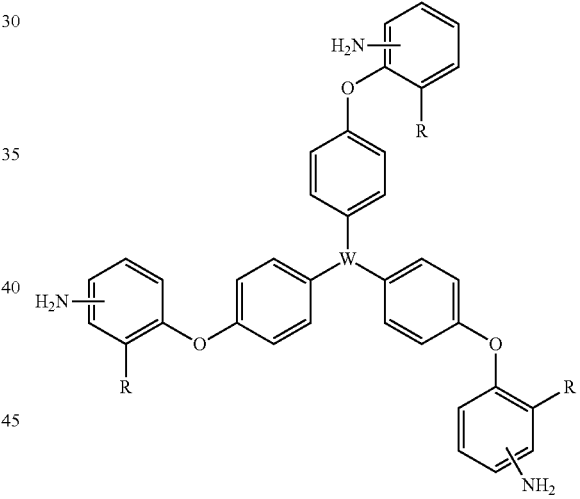

The crosslinked aromatic polyimides of the present invention have the following general formula, wherein Y is selected from the group consisting of —$C(CF_3)_2$—, —O—, —$SO_2$—, —C=O—, -(Ph)$C(CF_3)$—, —OPh-$C(CH_3)_2$-PhO—, —O(1,3-Ph)O— and —O(1,4-Ph)O—; and n, m, and l are degrees of polymerization of each branch of the crosslinked aromatic polyimide:

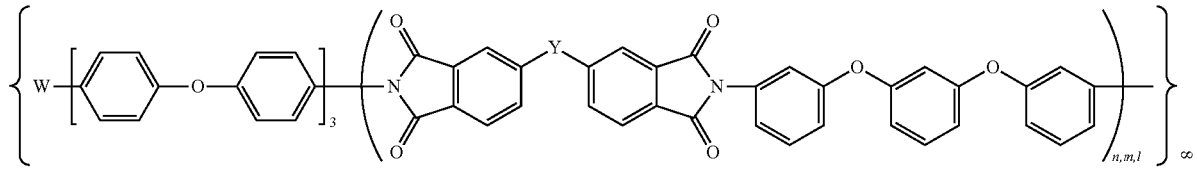

In one exemplary embodiment, the degrees of polymerization are the same with respect to one another. In another embodiment, at least one of the degrees of polymerization is different. In another embodiment, the degrees of polymerization comprise 10 to 110 units. In an alternative embodiment, the degrees of polymerization comprise 5 to 55 units.

In another exemplary embodiment, the tri(oxybenzene-amine) crosslinker comprises a concentration of 0.3-10 mol %. In another embodiment, the tri(oxybenzene-amine) crosslinker comprises a concentration of 0.5-5.0 mol %.

In another exemplary embodiment, the present invention includes a crosslinked aromatic polyimide in which the aromatic diamine is 1,3-bis(3-aminophenoxy)benzene; the dianhydride monomer is selected from the group consisting of 2,2-bis(phthalic anhydride)-1,1,1,3,3,3-hexafluoroisopropane, 4,4'-oxydi(phthalic anhydride), 3,3',4,4'-diphenylsulfone tetracarboxylic dianhydride, 3,3',4,4'-benzophenone tetracarboxylic dianhydride, 4,4'-(2,2,2-trifluoro-1-phenylethylidene)diphthalic anhydride, 2,2-bis[4-(3,4-dicarboxyphenoxy)phenyl]propane dianhydride, 4,4'-(p-phenylenedioxy)diphthalic anhydride, and 4,4'-(m-phenylenedioxy)diphthalic anhydride; and the tri(oxybenzene-amine) crosslinker is selected from the group consisting of 1,1,1-tris[4-(4-aminophenoxy)phenyl]ethane and tris[(4-aminophenoxy)phenyl]phosphine oxide.

In an alternative exemplary embodiment, the aromatic diamine is 1,3-bis(3-aminophenoxy)benzene, the dianhydride monomer is 2,2-bis(phthalic anhydride)-1,1,1,3,3,3-hexafluoroisopropane, and the tri(oxybenzene-amine) crosslinker is 1,1,1-tris[4-(4-aminophenoxy)phenyl]ethane. In another embodiment, the aromatic diamine is 1,3-bis(3-aminophenoxy)benzene, the dianhydride monomer is 2,2-bis(phthalic anhydride)-1,1,1,3,3,3-hexafluoroisopropane, and the tri(oxybenzene-amine) crosslinker is tris[(4-aminophenoxy)phenyl]phosphine oxide.

The present invention further includes a method for preparation of a crosslinked aromatic polyimide comprising the steps of: mixing at least one aromatic diamine and at least one dianhydride monomer in a polar solvent to form poly(amic acid) oligomers; adding a tri(oxybenzene-amine) crosslinker to the poly(amic acid) oligomers to form a sol-gel precursor; pouring the sol-gel precursor onto glass plates or petri dishes; and curing the sol-gel precursor to form the crosslinked aromatic polyimide having shape memory properties.

In one exemplary embodiment of the method, the aromatic diamine is 1,3-bis(3-aminophenoxy)benzene; the dianhydride monomer is selected from the group consisting of 2,2-bis(phthalic anhydride)-1,1,1,3,3,3-hexafluoroisopropane, 4,4'-oxydi(phthalic anhydride), 3,3',4,4'-diphenylsulfone tetracarboxylic dianhydride, 3,3',4,4'-benzophenone tetracarboxylic dianhydride, 4,4'-(2,2,2-trifluoro-1-phenylethylidene)diphthalic anhydride, 2,2-bis[4-(3,4-dicarboxyphenoxy)phenyl]propane dianhydride, 4,4'-(p-phenylenedioxy)diphthalic anhydride, and 4,4'-(m-phenylenedioxy)diphthalic anhydride; the polar solvent is selected from the group consisting of N,N-dimethylacetamide and N,N-dimethylformamide; and the tri(oxybenzene-amine) crosslinker is selected from the group consisting of 1,1,1-tris[4-(4-aminophenoxy)phenyl]ethane and tris[(4-aminophenoxy)phenyl]phosphine oxide.

In an alternative exemplary embodiment of the method, the aromatic diamine is 1,3-bis(3-aminophenoxy)benzene, the dianhydride monomer is 2,2-bis(phthalic anhydride)-1,1,1,3,3-hexafluoroisopropane, the polar solvent is N,N-dimethylacetamide, and the tri(oxybenzene-amine) crosslinker is 1,1,1-tris[4-(4-aminophenoxy)phenyl]ethane. In an alternative embodiment, the aromatic diamine is 1,3-bis(3-aminophenoxy)benzene, the dianhydride monomer is 2,2-bis(phthalic anhydride)-1,1,1,3,3,3-hexafluoroisopropane, the polar solvent is N,N-dimethylacetamide, and the tri(oxybenzene-amine) crosslinker is tris[(4-aminophenoxy)phenyl]phosphine oxide.

DETAILED DESCRIPTION OF THE INVENTION

Figure 1:
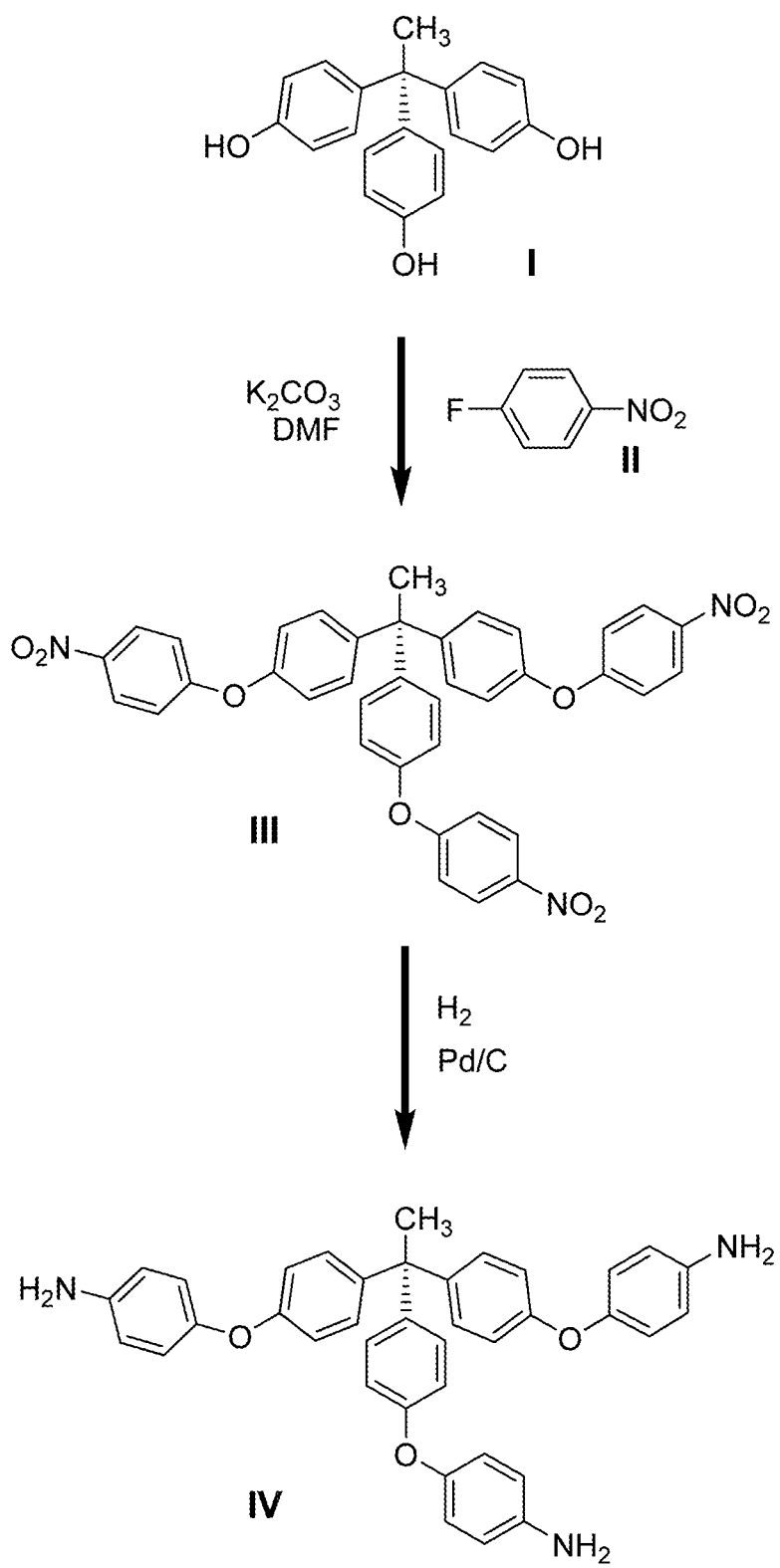
FIG. 1 illustrates the synthesis of an exemplary triamine crosslinker 1,1,1-tris[4-(4-aminophenoxy)phenyl]ethane (TAPE, IV) having the general structure A (W is $CH_3C$).

The present invention includes a crosslinked aromatic polyimide possessing shape memory properties and methods of making the same. The crosslinked aromatic polyimide comprises at least one aromatic diamine, at least one dianhydride monomer, and a tri(oxybenzene-amine) crosslinker. The resulting crosslinked polyimide polymers and films according to the present invention possess superior shape memory properties at elevated temperatures ranging from 228° C. to 246° C. The present invention further includes methods of making the same.

In general, polyimides display a unique combination of excellent mechanical, electrical, and optical properties, as well as superior thermal stability. Their monomers are also readily available or relatively easy to prepare compared to those of other high performance polymers. Thus, polyimides have found many applications in high performance films, fibers, adhesives, coatings, and laminates in many application areas such as microelectronics, optoelectronics, aerospace structural components, nonlinear-optical devices, light-wave guides, and liquid crystal displays.

CP2 (LaRC™-CP2, NASA Langley Research Center) is an exemplary fluorinated polyimide derived from 2,2-bis(phthalic anhydride)-1,1,1,3,3,3-hexafluoroisopropane (6FDA) and 1,3-bis(3-aminophenoxy)benzene (APB). CP2 is a high-performance aerospace-grade polyimide that possesses superior properties including high mechanical toughness, solvent resistance, high glass transition temperature, ultraviolet radiation resistance, and high thermal and thermo-oxidative stability. CP2 is also much more transparent than other polyimides and is generally pale yellow or colorless depending on the film thickness, giving it the additional properties of low solar absorption and higher resistance to degradation in harsh environments. It is particularly suitable for long-term survivability in space environments and has been used to develop lightweight, inflatable structures that serve as Gossamer-like spacecraft, satellites, and solar energy collection/reflection systems. Materials made from CP2 such as CP2 films possess shape memory properties and, like other polyimides, CP2 films have a relatively high $T_g$ as compared to other types of SMPs. When CP2 films are heated above their $T_g$ (about 199° C.), they may be stretched substantially and controllably to 0.5-2× their original length, and the shape change is kept by cooling the films below their $T_g$ under stress. When the stretched CP2 films are reheated above their $T_g$, they return to their original shape and size.

Other examples of suitable dianhydride monomers that may be used include 4,4'-oxydi(phthalic anhydride); 3,3',4,4'-diphenylsulfone tetracarboxylic dianhydride; 3,3',4,4'-benzophenone tetracarboxylic dianhydride; 4,4'-(2,2,2-trifluoro-1-phenylethylidene)diphthalic anhydride; 2,2-bis[4-(3,4-dicarboxyphenoxy)phenyl]propane dianhydride; 4,4'-(p-phenylenedioxy)diphthalic anhydride; and 4,4'-(m-phenylenedioxy)diphthalic anhydride.

The resulting crosslinked CP2 (i.e. xW-CP2) and related crosslinked polyimide polymers and films may comprise the following general structure B, in which Y may be —C(CF$_3$)$_2$—; —O—; —SO$_2$—; >C=O—; -(Ph)C(CF$_3$)—; —OPh-C(CH$_3$)$_2$-PhO—; —O(1,3-Ph)O—; or —O(1,4-Ph)O—:

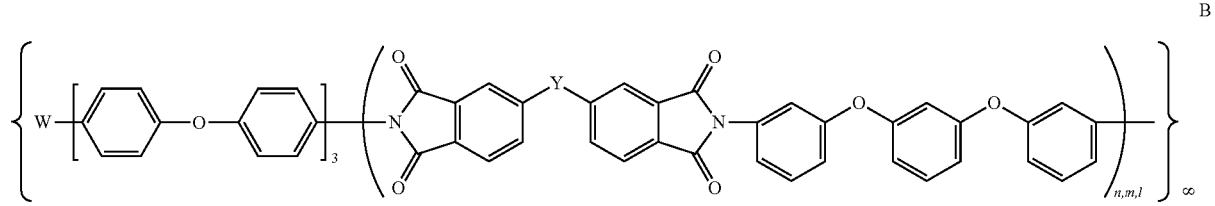

B

To improve the shape memory properties of CP2 and related polyimides, a crosslinker may be used to create crosslinked polyimide polymers and films. The crosslinker may include a multi(arylamine)-based or a multi(phthalic anhydride)-based compound having a degree of functionality that is equal to or greater than three. The use of tetrahedral geometry (free-volume consideration) and diphenylether linking groups provides both high-temperature tolerance and conformational flexibility.

A tri(oxybenzene-amine) crosslinker (also referred to herein as a triamine crosslinker) having the following general structure A may be used, in which W may be CH$_3$C (methylcarbyl); N (trivalent nitrogen); P=O (phosphine oxide); or BO$_3$ (borate); R may be H; F; Cl; CF$_3$; or CH$_3$; and the amine groups (—NH$_2$) may be in the meta or para position with respect to R:

A

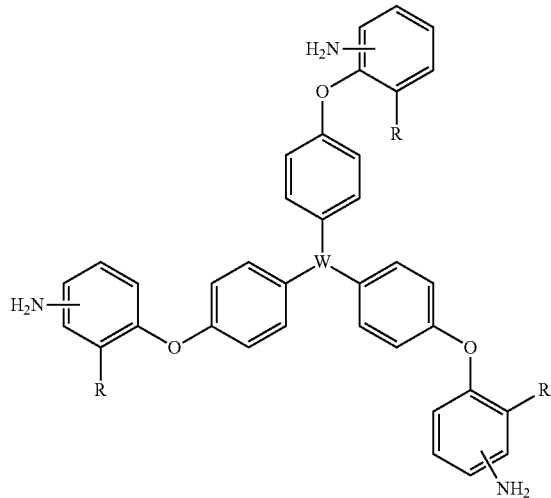

For clarity, "xW-CP2" is used herein as the generic designation for a polymer product having the general structure B that is derived from CP2 and a crosslinker of structure A with a "W" moiety. Thus, the specific designations are xE-CP2, where E is CH$_3$C; xPO-CP2, where PO is P=O; and so on. As used throughout, "Ph" refers to a phenyl (—C$_6$H$_5$) or a phenylene (—C$_6$H$_4$—) group.

The triamine crosslinker creates crosslinked polyimides containing three branches or spokes, with varying degrees of polymerization (DP) denoted as n, m, and 1. The DP represents the number of repeat units (contained in the brackets in the general structure B) that each branch contains. The DP values may be the same or different for each branch. In one embodiment, the DP may be between 10 and 110 units. In another embodiment, the DP may be between 5 and 55 units. The symbol ∞ is used to denote an infinite network structure for a crosslinked polymer.

The extent and amount of crosslinking in the crosslinked polyimide polymers and films may be altered by varying the concentration of the triamine crosslinker (i.e. 0.5, 1.0, 2.0, and 5.0 mol %; see Tables 1 and 2 below). In one embodiment, the triamine crosslinker concentration may vary from 0.3-10 mol %. In another embodiment, the triamine crosslinker concentration may be between 0.5-5 mol %. The ability to vary the amount of crosslinking allows the synthesis of crosslinked polyimides with mechanical properties (i.e. T$_g$) tailored to a specific application or to specific environmental conditions.

The present invention further includes methods of synthesizing crosslinked polyimides comprising the general steps of mixing one or more aromatic diamines and one or more dianhydride monomers in a polar solvent to form poly(amic acid) oligomers; adding a tri(oxybenzene-amine) crosslinker to the solution of poly(amic acid) oligomers to form a sol-gel precursor; pouring the sol-gel precursor onto glass plates or petri dishes; and curing the sol-gel precursor. The resulting crosslinked aromatic polyimides possess superior shape memory properties at elevated temperatures.

The following examples and methods are presented as illustrative of the present invention or methods of carrying out the invention, and are not restrictive or limiting of the scope of the invention in any manner Referring to the drawings, like reference numerals may designate like or corresponding parts throughout the several views.

Example 1

Synthesis of TNPE

The following is an exemplary procedure for the synthesis of 1,1,1-tris[4-(4-nitrophenoxy)phenyl]ethane (TNPE, III) as depicted in FIG. 1. 1,1,1-T is(4-hydroxyphenyl)ethane (THPE, I) (10.0 g, 33.0 mmol), 1-fluoro-4-nitrobenzene (II) (15.4 g, 109 mmol), potassium carbonate (15.1 g, 109 mmol), and DMF (100 mL) were combined and placed into a 250 mL three-necked flask equipped with a magnetic stir bar and nitrogen inlet and outlet. The mixture was stirred at room temperature for 24 hours before being filtered. The filtrate was diluted with ethyl acetate (400 mL), and the organic layer was separated. The organic layer was washed with water three times. It was dried over anhydrous magnesium sulfate and filtered. The filtrate was concentrated to 75 mL on a rotary evaporator, and then stored in a refrigerator for several days to afford 11.2 g (51%) of off-white crystals, m.p. 98-99° C. MS (m/e): 669 (M+). Anal. Calcd. for $C_{38}H_{27}N_3O_9$: C, 68.18%; H, 4.06%; N, 6.27%; O, 21.50%. Found: C, 67.69%; H, 4.26%; N, 6.21%; O, 21.22%. FT-IR (KBr, cm$^{-1}$): 3076, 2979, 1586, 1513, 1486, 1344, 1248, 1165, 1107, 874, 846. $^1$H-NMR (DMSO-$d_6$, δ in ppm): 2.26 (s, 3H, $CH_3$), 7.17-7.27 (m, 18H, Ar—H), 8.28-8.31 (d, 6H, Ar—H).

Example 2

Synthesis of TAPE

The following is an exemplary procedure for the synthesis of an exemplary triamine crosslinker 1,1,1-tris[4-(4-aminophenoxy)phenyl]ethane (TAPE, IV) by reduction of TNPE (III) via catalytic hydrogenation as depicted in FIG. 1. TNPE (III) (5.0 g, 7.5 mmol), THF (50 mL), and 5% palladium on activated carbon (0.50 g) were added to a hydrogenation bottle. The bottle was secured on a Parr hydrogenation apparatus, flushed three times with hydrogen, and then pressurized to 55 psi. After the mixture had been agitated at room temperature for 24 hours under the hydrogen pressure of 55 psi, it was filtered through Celite. The filter cake was washed with THF, and then the filtrate was evaporated to dryness on a rotary evaporator to afford a 4.25 g (98%) of yellow crystal, which was used without further purification, m.p. 220-221° C. MS (m/e): 579 (M+). Anal. Calcd. for $C_{38}H_{33}N_3O_3$: C, 78.73%; H, 5.74%; N, 7.25%. Found: C, 78.17%; H, 5.78%; N, 7.04%. FT-IR (KBr, cm$^{-1}$): 3441, 3361 ($NH_2$), 3035, 2970, 1617, 1581, 1497, 1384, 1232, 1173, 1117, 1010, 871, 842. $^1$H-NMR (DMSO-$d_6$, δ in ppm): 2.02 (s, 3H, $CH_3$), 4.99 (s, 6H, $NH_2$), 6.53-6.58 (d, 6H, Ar—H), 6.68-6.74 (m, 12H, Ar—H), 6.88-6.93 (d, 6H, Ar—H).

Example 3

Synthesis of xE-CP2 Films

Figure 2:
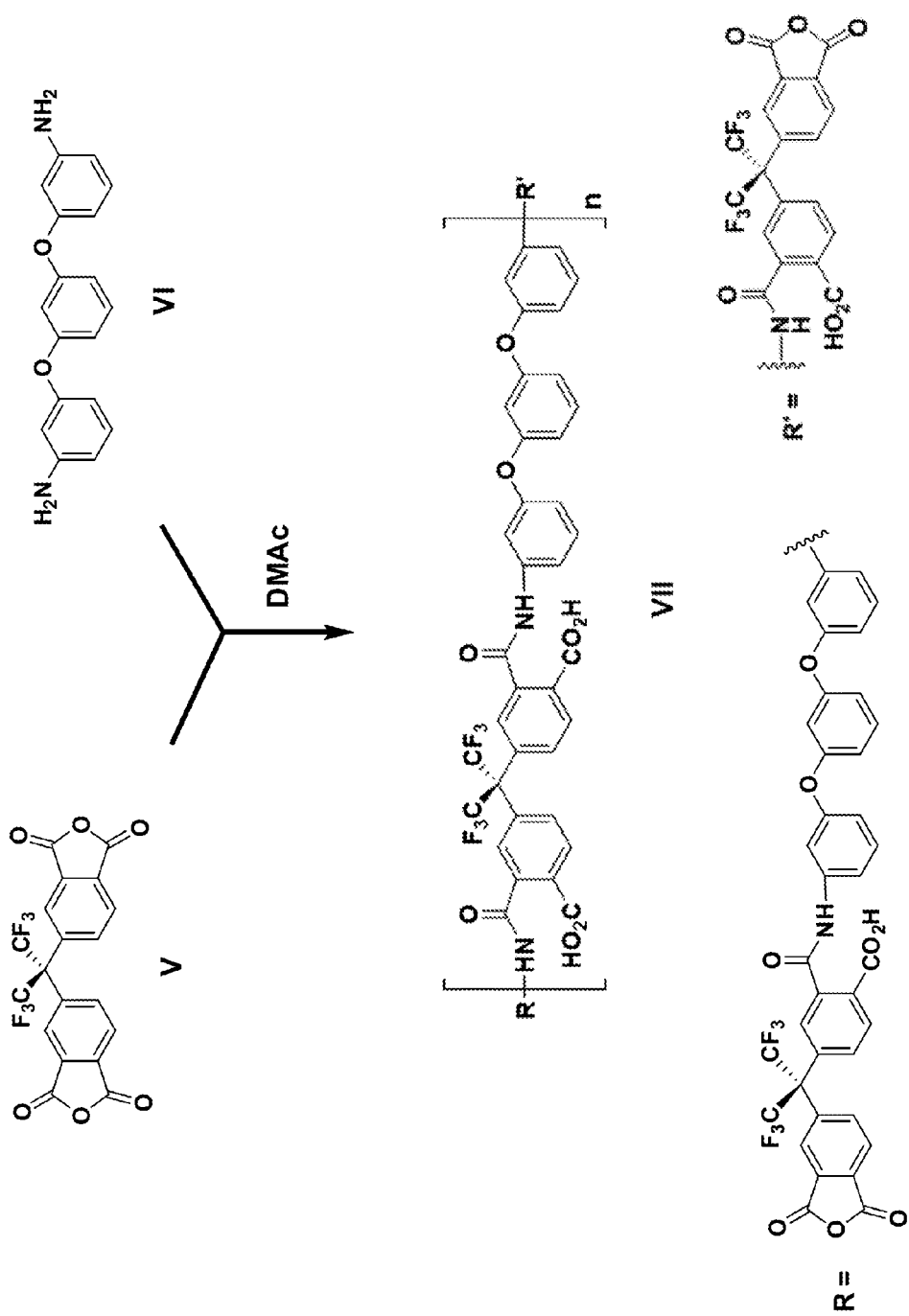
FIG. 2 illustrates an exemplary method of synthesizing dianhydride end-capped poly(amic acid) oligomers (PAA oligomers, VII).
Figure 3:
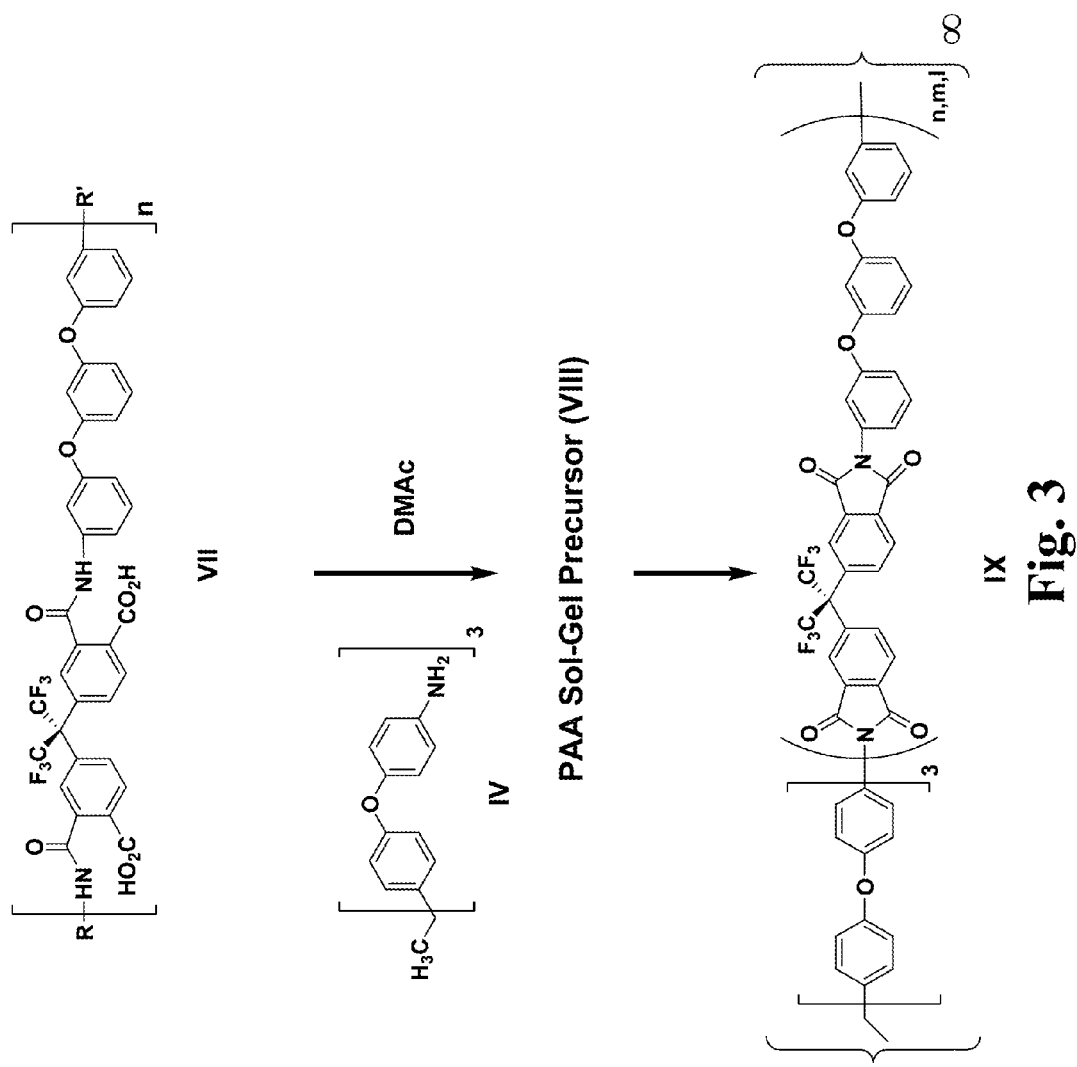
FIG. 3 illustrates an exemplary method of synthesizing crosslinked polyimides (xE-CP2, IX) comprising the triamine crosslinker 1,1,1-tris[4-(4-aminophenoxy)phenyl]ethane (TAPE, IV) of FIG. 1 and the dianhydride end-capped poly(amic acid) oligomers (VII) of FIG. 2.

The following is an exemplary procedure for the synthesis of xE-CP2 polyimide films (IX, collectively referred to as xE-CP2) (5 mol %) as depicted in FIGS. 2 and 3 and as the xE-CP2-5.0 sample in Table 1. APB (VI) (1.081 g, 3.700 mmol) and DMAc (14 mL) were added to a 50 mL three-necked flask equipped with a magnetic stirrer and a nitrogen inlet and outlet and stirred under dry nitrogen at room temperature for 30 minutes. An excess of 6FDA (V) (1.777, 4.000 mmol) was then introduced to the resulting solution. The light yellow solution was agitated at room temperature for 24 hours to afford a solution of poly(amic acid) oligomers (PAA oligomers, VII) as shown in FIG. 2. As shown in FIG. 3, TAPE (IV) (0.1159 g, 0.200 mmol) synthesized according to FIG. 1 and Examples 1 and 2 was added to the solution of PAA oligomers (VII) in DMAc. For clarity, only the three terminal amine groups of the triamine crosslinker TAPE (IV) are depicted in FIG. 3. After the TAPE (IV) had completely dissolved, the resulting PAA sol-gel precursor solution (VIII, structure not shown) was poured into a glass petri dish, followed by vacuum evaporation of the DMAc at 50° C. and heat-treatment according to following schedule: 100° C./2 hours, 150° C./2 hours, 175° C./1 hour, 200° C./2 hours, 250° C./1 hour, and 300° C./1 hour to form films consisting of xE-CP2 (IX). The resulting film thickness was approximately 20-100 μm.

The procedures depicted in FIGS. 1-3 and described in Examples 1-3 were used to prepare exemplary crosslinked CP2 polyimide films (xE-CP2 films) having general structure B based on the triamine crosslinker TAPE having the general structure A, the properties of which are detailed below in Table 1. The concentration of TAPE may be varied in the xE-CP2 films by adding various amounts (i.e. 0.5, 1.0, 2.0, and 5.0 mol %) of TAPE to the respective PAA/DMAc solutions. The molar ratios of the three monomer mixtures, 6FDA:APB:TAPE, are listed in Table 1. The swelling tests were conducted in DMAc. Dry films were weighed before being submerged in DMAc for three days. The swollen films were taken out and weighed, and they were dried in an oven up to 300° C. to remove the DMAc. The dried films were then weighed again.

TABLE 1 xE-CP2 Films

| Sample | 6FDA (mol %) | APB (mol %) | TAPE (mol %) | $T_g$ (° C.) | E (GPa) | $M_c$ (Dalton) | Swelling Ratio | Gel Content (%) |
|---|---|---|---|---|---|---|---|---|
| CP2 | 100 | 100 | 0 | 219 | 1.9 | — | — | — |
| xE-CP2-0.5 | 100 | 99.75 | 0.5 | 232 | 1.5 | 78,910 | 10.34 | 56.2 |
| xE-CP2-1.0 | 100 | 98.5 | 1.0 | 234 | 1.7 | 48,372 | 6.87 | 68.7 |
| xE-CP2-2.0 | 100 | 97.0 | 2.0 | 235 | 1.3 | 33,037 | 4.64 | 93.3 |
| xE-CP2-5.0 | 100 | 92.5 | 5.0 | 239 | 1.2 | 7,030 | 3.29 | 100 |

In Table 1, the glass transition temperature ($T_g$) is measured from the peak or tan delta as an average value taken from four measurements during dynamic mechanical analysis (DMA). The tensile modulus (E) was determined in tension at 25° C. as an average from five specimens per sample. $M_c$ denotes the average molecular weight of the linear segment between two crosslinked sites, calculated from the following equation: $M_c=350.27\times X_n+191.21\times 2$, where 350.27 is one-half the formula weight of a CP2 repeat unit; the number-average degree of polymerization $X_n=(1+r)/(1-r)$; the stoichiometric imbalance factor (r) is the molar ratio of diamine to dianhydride; and 191.21 is one-third of the value of the formula weight of a crosslinker segment (from methyl-end to imide-nitrogen) in the xE-CP2 network. The Swelling Ratio was determined by the following equation: (dry sample weight+DMAc weight)/dry sample weight. The Gel Content was based on the dried insoluble polyimide in DMAc.

As seen in Table 1, while the crosslinking density increases as the concentration of TAPE increases, the calculated average molecular weights between crosslinked sites ($M_c$) follows an opposite trend. The $T_g$ of neat polyimide (CP2) is 219° C. by DMA. Comparatively, the $T_g$ values (232-239° C.) of the xE-CP2 films increase with the concentration of TAPE. Also as seen in Table 1, the tensile moduli (E) of the xE-CP2 films are lower than that of the unaltered or neat CP2 for the amount of the crosslinker (0.5-5 mol %) added. It is likely that at the TAPE concentration of ≤5 mol %, the tripod geometry of TAPE may be disrupting the chain-packing regularity of the CP2 polyimide, resulting in softening of the polymer networks in the xE-CP2 films. Finally, the Swelling Ratios decreased with crosslinking density, while gel contents increased. When the crosslinking density of the xE-CP2 films is low, they can uptake as much as 90% w/w of water in their interstitial space.

Example 4

Synthesis of a Hollow Object Comprising xE-CP2

The following is a representative procedure for fabrication of a hollow object from xE-CP2 polyimide comprising 5 mol % TAPE (IV) synthesized as shown in FIGS. 1-3 and Examples 1-3. APB (VI) (1.081 g, 3.700 mmol) and DMAc (10 mL) were added to a 50 mL three-necked flask equipped with a magnetic stirrer and a nitrogen inlet and outlet and stirred under dry nitrogen at room temperature for 30 minutes. 6FDA (V) (1.777 g, 4.000 mmol) was then introduced to the resulting solution. The light yellow solution was agitated at room temperature for 24 hours to afford a poly(amic acid) oligomer solution (VII). Then, the triamine crosslinker TAPE (IV) (0.1159 g, 0.200 mmol) was added to this solution. After the TAPE (IV) had completely dissolved in the DMAc, the resulting PAA sol-gel precursor solution (VIII, structure not shown) was poured into a 50 mL glass flask with a ground joint mouth. The flask was rotated on a rotary evaporator at the highest rotating speed while also being warmed with a heat gun until most of the solvent (DMAc) was stripped off under reduced pressured (assisted by a water aspirator). Eventually, the solidified crosslinked PAA sol-gel (VIII) covered the internal wall of the flask, forming a hollow object that assumed the shape of the flask. The flask coated with the PAA sol-gel precursor (VIII) was then heat-treated according to following schedule: 100° C./2 hours, 150° C./2 hours, 175° C./1 hour, 200° C./2 hours, 250° C./1 hour, and 300° C./1 hour to form a robust polyimide film on the flask walls. After the flask had been allowed to cool to room temperature, water was added to the flask to de-bond the crosslinked polyimide film from the internal walls of the flask. The water was then poured out, and the glass flask was carefully broken to allow the retrieval of the xE-CP2-5.0 polyimide "flask." The film thickness was approximately 50 µm. The polyimide flask displayed excellent shape memory effect. It could be squarely compressed under a suitable load (e.g. a Teflon® plate) and decompressed (without load) at the switching temperature of ca. 240° C. The compressed shape was retained after removal from the oven and held indefinitely until the flask was placed in an oven set at 240° C., at which temperature the original flask shape was nearly restored.

Example 5

Synthesis of TMPO

Figure 4:
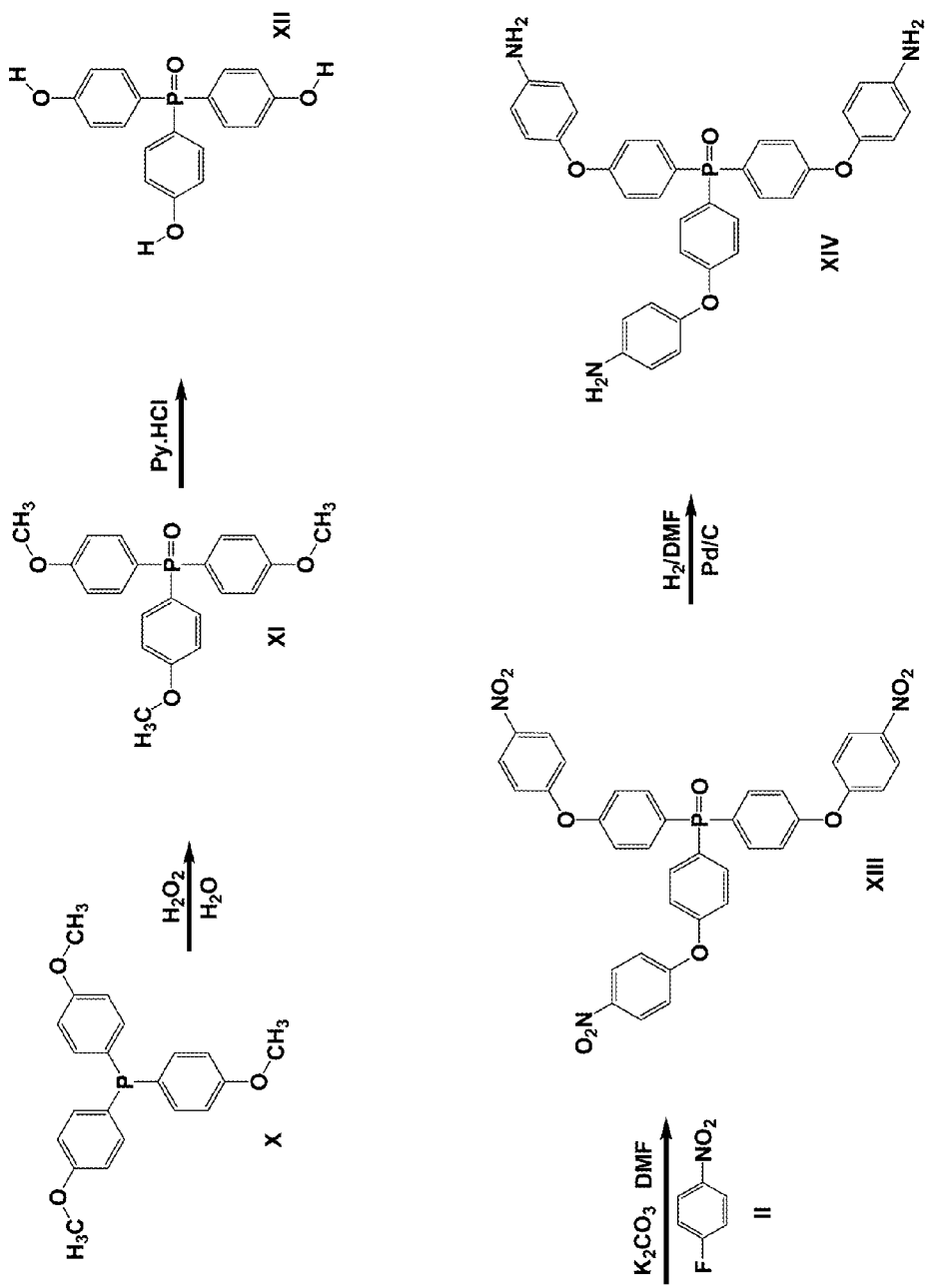
FIG. 4 illustrates the synthesis of another exemplary triamine crosslinker tris[(4-aminophenoxy)phenyl]phosphine oxide (TAPO, XIV) having the general structure A (W is $P=O$).

The following is an exemplary procedure for the synthesis of tris(4-methoxyphenyl)phosphine oxide (TMPO, XI) as depicted in FIG. 4. Into a 100 mL three-necked flask equipped with a magnetic stir bar and nitrogen inlet and outlet were placed tris(4-methoxyphenyl)phosphine (TMP, X) (3.0 g, 8.5 mmol) and acetone (30 mL). A mixture of water (2 mL) and $H_2O_2$ (35%, 1 mL, 9 mmol) was added slowly. After the mixture had been stirred at room temperature for 1 hour, the acetone was evaporated, and methylene chloride (50 mL) was added. The organic phase was washed with a saturated NaCl solution (35 mL) three times with the aid of a separatory funnel. The organic layer was then dried over anhydrous sodium sulfate. Finally, the solvent was removed via rotary evaporation to afford 3.0 g (95%) of a white solid, m.p. 144.7-145.4° C. MS (m/e): 368 ($M^+$). Anal. Calcd. for $C_{21}H_{21}O_4P$: C, 68.47%; H, 5.75%; P, 8.41%. Found: C, 68.42%; H, 5.72%; P, 8.11%. FT-IR (KBr, $cm^{-1}$): 3068, 3026, 2959, 2837, 1597, 1569, 1503, 1468, 1289, 1254, 1179, 1121, 1019, 803, 671, 543. $^1$H-NMR ($CDCl_3$, δ in ppm): 3.84 (s, 6H, $CH_3$), 6.94-6.97 (dd, 6H, Ar—H), 7.54-7.60 (dd, 6H, Ar—H). $^{13}$C-NMR (DMSO-$d_6$, δ in ppm): 55.29, 114.08, 114.21, 124.19, 125.28, 133.21, 133.32, 161.79, 161.82.

Example 6

Synthesis of THPO

The following is an exemplary procedure for the synthesis of tris(4-hydroxyphenyl)phosphine oxide (THPO, XII) via demethylation of TMPO (XI) as depicted in FIG. 4. Into a 500 mL three-necked flask equipped with a magnetic stir bar and nitrogen inlet and outlet were placed TMPO (XI) (25.0 g, 67.9 mmol) and pyridine hydrochloride (250 g) at 210° C. for 2 hours. The light brown solution was poured into water while it was still hot. The white precipitate was collected and recrystallized from ethyl acetate to afford 21.0 g (95%) of white crystals, m.p. 274.8-276.8° C. MS (m/e): 326 ($M^+$). FT-IR (KBr, $cm^{-1}$): 3380, 1601, 1581, 1505, 1436, 1278, 1175, 1119, 1068, 831, 677, 537. $^1$H-NMR (DMSO-$d_6$, δ in ppm): 6.86-6.89 (dd, 6H, Ar—H), 7.32-7.38 (dd, 6H, Ar—H), 10.14 (s, 3H, OH). $^{13}$C-NMR (DMSO-$d_6$, δ in ppm): 115.32, 115.45, 122.59, 123.69, 133.29, 133.40, 160.28, 160.30.

Example 7

Synthesis of TNPO

The following is an exemplary procedure for the synthesis of tris[(4-nitrophenoxy)phenyl]phosphine oxide (TNPO, XIII) as depicted in FIG. 4. Into a 250 mL three-necked flask equipped with a magnetic stir bar and nitrogen inlet and outlet were placed THPO (XII) (7.52 g, 20.0 mmol), 1-fluoro-4-nitrobenzene (II) (9.32 g, 66.0 mmol), potassium carbonate (9.14 g, 66.0 mmol), and DMF (100 mL) at 100° C. for 48 hours. The mixture was allowed to cool to room temperature and filtered. The filtrate was poured into water, and the precipitate was extracted with ethyl acetate (300 mL) three times with the aid of a separatory funnel. The combined organic extract was concentrated under vacuum, and 13.3 g (97%) of yellow crystals that were formed during the concentrating process was collected by filtration, m.p. 205.0-206.6° C. MS (m/e): 689 (M$^+$). FT-IR (KBr, cm$^{-1}$): 3071, 1612, 1585, 1523, 1487, 1345, 1242, 1176, 1116, 879, 866, 831, 788, 696, 556. $^1$H-NMR (DMSO-d$_6$, 6 in ppm): 7.27-7.31 (d, 6H, Ar—H), 7.35-7.37 (d, 6H, Ar—H), 7.75-7.80 (m, 6H, Ar—H), 8.27-8.31 (d, 6H, Ar—H). $^{13}$C-NMR (DMSO-d$_6$, δ in ppm): 118.84, 119.82, 119.94, 126.22, 128.18, 129.23, 134.09, 134.20, 143.09, 157.93, 157.96, 161.29.

Example 8

Synthesis of TAPO

The following is an exemplary procedure for the synthesis of another exemplary triamine crosslinker tris[(4-aminophenoxy)phenyl]phosphine oxide (TAPO, XIV) having the general structure A where W is P=O (IUPAC name 4,4',4''-(4,4',4''-phosphinetriyltris(benzene-4,1-diyl)tris(oxy)) trianiline) by reduction of TNPO (XIII) via catalytic hydrogenation as depicted in FIG. 4. TNPO (XIII) (8.0 g, 11.6 mmol), DMF (120 mL), and 5% palladium on activated carbon (0.50 g) were added to a hydrogenation bottle. The bottle was secured on a Parr hydrogenation apparatus, flushed three times with hydrogen, and then pressurized to 60 psi. After the mixture had been agitated at room temperature for 24 hours under hydrogen pressure of 60 psi, it was filtered through a cake of Celite. The filter cake was washed with DMF. The filtrate was then poured into water to precipitate a white solid that was subsequently recrystallized from ethanol/water to afford 6.41 g (98%) of white crystal, m.p. 211.1-211.5° C. MS (m/e): 559 (M$^+$). Anal. Calcd. for $C_{36}H_{30}N_3O_4P$: C, 72.11%; H, 5.04%; N, 7.01%. Found: C, 72.01%; H, 4.97%; N, 6.91%. FT-IR (KBr, cm$^{-1}$): 3437, 3328, 3210, 3042, 1592, 1507, 1493, 1242, 1197, 1165, 1117, 871, 830, 671, 577. $^1$H-NMR (DMSO-d$_6$, δ in ppm): 5.06 (s, 6H, NH$_2$), 6.59-6.62 (d, 6H, Ar—H), 6.79-6.81 (d, 6H, Ar—H), 6.94-6.96 (d, 6H, Ar—H), 7.48-7.53 (d, 6H, Ar—H). $^{13}$C-NMR (DMSO-d$_6$, δ in ppm): 114.85, 115.89, 116.01, 121.34, 125.06, 126.13, 133.40, 133.51, 144.11, 146.13, 162.89, 161.92.

Example 9

Synthesis of xPO-CP2 Films

Figure 5:
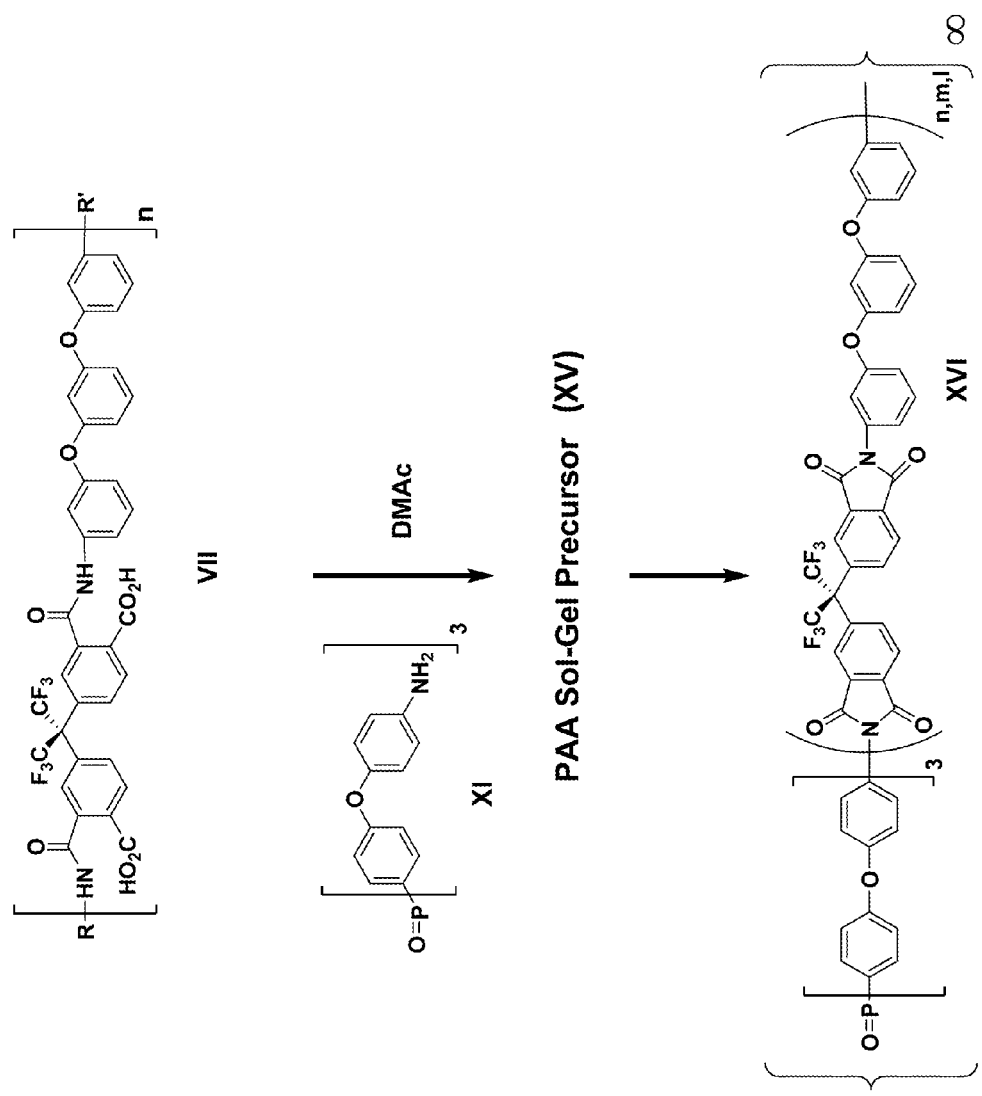
FIG. 5 illustrates another exemplary method of synthesizing crosslinked polyimides (xPO-CP2, XVI) comprising the triamine crosslinker tris[(4-aminophenoxy)phenyl]phosphine oxide (TAPO, XIV) of FIG. 4 and the dianhydride end-capped poly(amic acid) oligomers (VII) of FIG. 2.

The following is an exemplary procedure for the synthesis of crosslinked xPO-CP2 polyimide films (XVI, collectively referred to as xPO-CP2) with 5 mol % crosslinker TAPO (XIV) as depicted in FIG. 5 and as the xPO-CP2-5.0 sample in Table 2. APB (VI) (1.081 g, 3.700 mmol) and DMAc (14 mL) were added to a 50 mL three-necked flask equipped with a magnetic stirrer and a nitrogen inlet and outlet and stirred under dry nitrogen at room temperature for 30 minutes. 6FDA (V) (1.777 g, 4.000 mmol) was then introduced to the resulting solution. The light yellow solution was agitated at room temperature for 24 hours to afford a dianhydride end-capped poly(amic acid) oligomer solution (VII) shown in FIG. 2. The triamine crosslinker TAPO (XIV) (0.1200 g, 0.200 mmol) synthesized according to FIG. 4 and Examples 5-8 was then added to this solution. For clarity, only the three terminal amine groups of the triamine crosslinker TAPO (XIV) are depicted in FIG. 5. After the TAPO (XIV) had completely dissolved in the DMAc, the resulting PAA sol-gel precursor (XV, structure not shown) was poured into a glass petri dish, followed by vacuum evaporation of the DMAc at 50° C. and heat-treatment according to the following schedule: 100° C./2 hours, 150° C./2 hours, 175° C./1 hour, 200° C./2 hours, 250° C./1 hour, and 300° C./1 hour to form xPO-CP2 polyimide films (XVI). The film thickness was approximately 20-100 μm. ATR-IR (Film, cm$^{-1}$): 3076, 1784, 1720, 1586, 1478, 1449, 1368, 1298, 1239, 1189, 1141, 1098, 1003, 846, 811, 779, 718, 681, 627, 568.

The procedures illustrated in FIGS. 4-5 and Examples 5-9 were used to prepare crosslinked CP2 polyimide films (xPO-CP2 films) having the general structure B based on the triamine crosslinker TAPO having the general structure A, the properties of which are detailed below in Table 2. The concentration of TAPO may be varied in the xPO-CP2 films by adding various amounts (i.e. 1.0, 2.0, and 5.0 mol %) of TAPO to the respective PAA/DMAc solutions. The molar ratios of the three monomer mixtures, 6FDA:APB:TAPO, are listed in Table 2. The swelling tests were conducted in DMAc. Dry films were weighed before being submerged in DMAc for three days. The swollen films were taken out and weighed, and they were dried in an oven up to 300° C. to remove the DMAc. The dried films were then weighed again.

TABLE 2

| | xPO-CP2 Films | | | | | | | |
|---|---|---|---|---|---|---|---|---|
| Sample | 6FDA (mol %) | APB (mol %) | TAPO (mol %) | $T_g$ (° C.) | E (GPa) | $M_c$ (Dalton) | Swelling Ratio | Gel Content (%) |
| CP2 | 100 | 100 | 0 | 219 | 1.9 | — | — | — |
| xPO-CP2-1.0 | 100 | 98.5 | 1.0 | 228 | 2.5 | 46,680 | 11.5 | 74.5 |
| xPO-CP2-2.0 | 100 | 97.0 | 2.0 | 232 | 2.7 | 23,350 | 4.60 | 96.6 |
| xPO-CP2-5.0 | 100 | 92.5 | 5.0 | 246 | 3.2 | 9,350 | 3.02 | 98.8 |

In Table 2, the glass transition temperature ($T_g$) is measured from the peak or tan delta as an average value taken from four measurements during dynamic mechanical analysis (DMA). The tensile modulus (E) was determined in tension at 25° C. as an average from five specimens per sample. $M_c$ denotes the average molecular weight of the linear segment between two crosslinked sites, calculated from the following equation: $M_c=350.27 \times X_n+192.52 \times 2$, where 350.27 is one-half the formula weight of a CP2 repeat unit; the number-average degree of polymerization $X_n=(1+r)/(1-r)$; the stoichiometric imbalance factor (r) is the molar ratio of diamine to dianhydride; and 192.52 is one-third of the value of the formula weight of a crosslinker segment (from PO-end to imide-nitrogen) in the xPO-CP2 network. The Swelling Ratio was determined by the following equation: (dry sample weight+DMAc weight)/dry sample weight. The Gel Content was based on the dried insoluble polyimide in DMAc.

As seen in Table 2, while the crosslinking density increases as the concentration of TAPO increases, the calculated average molecular weights between crosslinked sites ($M_c$) follows an opposite trend. The $T_g$ of neat polyimide (CP2) is 219° C. by DMA. Comparatively, the $T_g$ values (228-246° C.) of the xPO-CP2 films increase with the concentration of TAPO. Unlike the xE-CP2 films in Table 1, the tensile moduli (E) of the xPO-CP2 films in Table 2 increase as the amount of crosslinker increases. Finally, the Swelling Ratios decreased with crosslinking density, while gel contents increased.

Although this invention has been described with respect to certain embodiments, various other embodiments and various changes and modifications to the disclosed embodiment(s) will become apparent to those skilled in the art. All such other embodiments, changes, and modifications are intended to come within the spirit and scope of the appended claims.

What is claimed is:

1. A crosslinked aromatic polyimide having shape memory properties, the crosslinked aromatic polyimide comprising:
    at least one aromatic diamine;
    at least one dianhydride monomer; and
    a tri(oxybenzene-amine) crosslinker having the general formula:

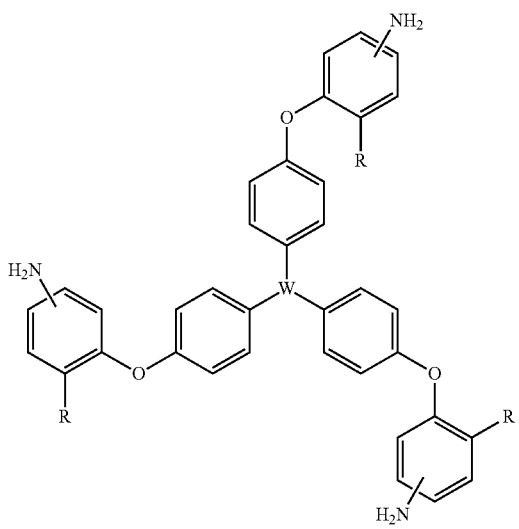

wherein W is selected from a group consisting of N, P=O, or $BO_3$; R is selected from a group consisting of H, F, Cl, $CF_3$, or $CH_3$; and the amine groups are located meta or para with respect to R, the crosslinked aromatic polyimide having the general formula:

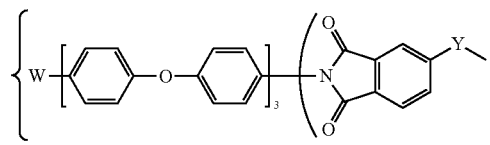

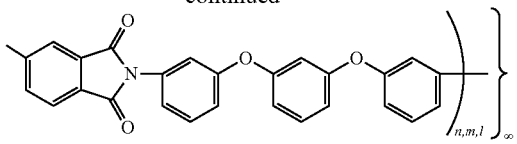

wherein Y is selected from the group consisting of —C(CF$_3$)$_2$—, —O—, —SO$_2$—, >C=O—, -(Ph)C(CF$_3$)—, —OPh-C(CH$_3$)$_2$-PhO—, —O(1,3-Ph)O— and —O(1,4-Ph)O—; and n, m, and l are degrees of polymerization of each branch of the crosslinked aromatic polyimide.

2. The crosslinked aromatic polyimide of claim 1 wherein the degrees of polymerization are the same with respect to one another.

3. The crosslinked aromatic polyimide of claim 1 wherein at least one of the degrees of polymerization is different.

4. The crosslinked aromatic polyimide of claim 1 wherein the degrees of polymerization comprise 10 to 110 units.

5. The crosslinked aromatic polyimide of claim 1 wherein the degrees of polymerization comprise 5 to 55 units.

6. The crosslinked aromatic polyimide of claim 1 wherein the tri(oxybenzene-amine) crosslinker comprises a concentration of 0.3-10 mol %.

7. The crosslinked aromatic polyimide of claim 1 wherein the tri(oxybenzene-amine) crosslinker comprises a concentration of 0.5-5.0 mol %.

8. The crosslinked aromatic polyimide of claim 1 wherein the aromatic diamine is 1,3-bis(3-aminophenoxy)benzene;
    the dianhydride monomer is selected from the group consisting of 2,2-bis(phthalic anhydride)-1,1,1,3,3,3-hexafluoroisopropane, 4,4'-oxydi(phthalic anhydride), 3,3',4,4'-diphenylsulfone tetracarboxylic dianhydride, 3,3',4,4'-benzophenone tetracarboxylic dianhydride, 4,4'-(2,2,2-trifluoro-1-phenylethylidene)diphthalic anhydride, 2,2-bis[4-(3,4-dicarboxyphenoxy)phenyl]propane dianhydride, 4,4'-(p-phenylenedioxy)diphthalic anhydride, and 4,4'-(m-phenylenedioxy)diphthalic anhydride; and
    the tri(oxybenzene-amine) crosslinker is selected from the group consisting of tris[(4-aminophenoxy)phenyl]amine, tris[(2-chloro-4-aminophenoxy)phenyl]-amine, tris[(2-fluoro-4-aminophenoxy)phenyl]amine, tris[(2-methyl-4-aminophenoxy)phenyl]amine, tris[(2-trifluoromethyl-4-aminophenoxy)phenyl]amine, tris[(2-chloro-5-aminophenoxy)phenyl]amine, tris[(2-chloro-5-aminophenoxy)phenyl]amine, tris[(2-chloro-5-aminophenoxy)phenyl]amine, tris[(2-fluoro-5-aminophenoxy)phenyl]amine, tris[(2-methyl-5-aminophenoxy)phenyl]amine, tris[(2-trifluoromethyl-5-aminophenoxy)phenyl]amine.

9. The crosslinked aromatic polyimide of claim 1 wherein the aromatic diamine is 1,3-bis(3-aminophenoxy)benzene;
    the dianhydride monomer is selected from the group consisting of 2,2-bis(phthalic anhydride)-1,1,1,3,3,3-hexafluoroisopropane, 4,4'-oxydi(phthalic anhydride), 3,3',4,4'-diphenylsulfone tetracarboxylic dianhydride, 3,3',4,4'-benzophenone tetracarboxylic dianhydride, 4,4'-(2,2,2-trifluoro-1-phenylethylidene)diphthalic anhydride, 2,2-bis[4-(3,4-dicarboxyphenoxy)phenyl]propane dianhydride, 4,4'-(p-phenylenedioxy)diphthalic anhydride, and 4,4'-(m-phenylenedioxy)diphthalic anhydride; and
    the tri(oxybenzene-amine) crosslinker is selected from the group consisting of tris[(4-aminophenoxy)phenyl]borate, tris[(2-chloro-4-aminophenoxy)phenyl]borate, tris [(2-chloro-4-aminophenoxy)phenyl]borate, tris[(2-fluoro-4-aminophenoxy)phenyl]borate, tris[(2-methyl-4-aminophenoxy)phenyl]borate, tris[(2-trifluoromethyl-4-aminophenoxy)phenyl]borate, tris [(2-chloro-5-aminophenoxy)phenyl]borate, tris[(2-fluoro-5-aminophenoxy)phenyl]borate, tris[(2-trifluoromethyl-5-aminophenoxy)phenyl]borate.

10. The crosslinked aromatic polyimide of claim 1 wherein the aromatic diamine is 1,3-bis(3-aminophenoxy)benzene;
the dianhydride monomer is selected from the group consisting of 2,2-bis(phthalic anhydride)-1,1,1,3,3,3-hexafluoroisopropane, 4,4'-oxydi(phthalic anhydride), 3,3',4,4'-diphenylsulfone tetracarboxylic dianhydride, 3,3',4,4'-benzophenone tetracarboxylic dianhydride, 4,4'-(2,2,2-trifluoro-1-phenylethylidene)diphthalic anhydride, 2,2-bis[4-(3,4-dicarboxyphenoxy)phenyl] propane dianhydride, 4,4'-(p-phenylenedioxy)diphthalic anhydride, and 4,4'-(m-phenylenedioxy)diphthalic anhydride; and
the tri(oxybenzene-amine) crosslinker is tris[(4-aminophenoxy)phenyl]phosphine oxide, tris[(4-aminophenoxy)phenyl]phosphine oxide, tris[(2-fluoro-4-aminophenoxy)phenyl]phosphine oxide, tris[(2-methyl-4-aminophenoxy)phenyl]phosphine oxide, tris[(2-trifluoromethyl-4-aminophenoxy)phenyl]phosphine oxide, tris[(2-chloro-5-aminophenoxy)phenyl]phosphine oxide, tris[(2-trifluoromethyl-5-aminophenoxy)phenyl]phosphine oxide, tris[(2-methyl-5-aminophenoxy)phenyl]phosphine oxide, tris[(2-fluoro-5-aminophenoxy)phenyl]phosphine oxide.

11. The crosslinked aromatic polyimide of claim 10 wherein the aromatic diamine is 1,3-bis(3-aminophenoxy) benzene, the dianhydride monomer is 2,2-bis(phthalic anhydride)-1,1,1,3,3,3-hexafluoroisopropane, and the tri(oxybenzene-amine) crosslinker is tris[(4-aminophenoxy)phenyl] phosphine oxide.

12. A method for preparation of a film comprising the crosslinked aromatic polyimide of claim 1 comprising the steps of:
mixing at least one aromatic diamine and at least one dianhydride monomer in a polar solvent to form poly (amic acid) oligomers;
adding a solid tri(oxybenzene-amine) crosslinker to the poly(amic acid) oligomers to form a soluble sol-gel precursor;
pouring the soluble sol-gel precursor onto glass plates or petri dishes; and
curing and crosslinking by simultaneously heating and removing the polar solvent from the soluble sol-gel precursor to form the crosslinked aromatic polyimide having shape memory properties.

13. The method of claim 12 wherein the aromatic diamine is 1,3-bis(3-aminophenoxy)benzene;
the dianhydride monomer is selected from the group consisting of 2,2-bis(phthalic anhydride)-1,1,1,3,3,3-hexafluoroisopropane, 4,4'-oxydi(phthalic anhydride), 3,3',4,4'-diphenylsulfone tetracarboxylic dianhydride, 3,3',4,4'-benzophenone tetracarboxylic dianhydride, 4,4'-(2,2,2-trifluoro-1-phenylethylidene)diphthalic anhydride, 2,2-bis[4-(3,4-dicarboxyphenoxy)phenyl] propane dianhydride, 4,4'-(p-phenylenedioxy)diphthalic anhydride, and 4,4'-(m-phenylenedioxy)diphthalic anhydride;
the polar solvent is selected from the group consisting of N,N-dimethylacetamide and N,N-dimethylformamide; and
the tri(oxybenzene-amine) crosslinker is selected from the group consisting of tris[(4-aminophenoxy)phenyl] amine, tris[(2-chloro-4-aminophenoxy)phenyl]amine, tris[(2-fluoro-4-aminophenoxy)phenyl]amine, tris[(2-methyl-4-aminophenoxy)phenyl]amine, tris[(2-trifluoromethyl-4-aminophenoxy)phenyl]amine, tris[(2-chloro-5-aminophenoxy)phenyl]amine, tris[(2-chloro-5-aminophenoxy)phenyl]amine, tris[(2-chloro-5-aminophenoxy)phenyl]amine, tris[(2-fluoro-5-aminophenoxy)phenyl]amine, tris[(2-methyl-5-aminophenoxy)phenyl]amine, tris[(2-trifluoromethyl-5-aminophenoxy)phenyl]amine.

14. The method of claim 12 wherein the aromatic diamine is 1,3-bis(3-aminophenoxy)benzene;
the dianhydride monomer is selected from the group consisting of 2,2-bis(phthalic anhydride)-1,1,1,3,3,3-hexafluoroisopropane, 4,4'-oxydi(phthalic anhydride), 3,3',4,4'-diphenylsulfone tetracarboxylic dianhydride, 3,3',4,4'-benzophenone tetracarboxylic dianhydride, 4,4'-(2,2,2-trifluoro-1-phenylethylidene)diphthalic anhydride, 2,2-bis[4-(3,4-dicarboxyphenoxy)phenyl] propane dianhydride, 4,4'-(p-phenylenedioxy)diphthalic anhydride, and 4,4'-(m-phenylenedioxy)diphthalic anhydride;
the polar solvent is selected from the group consisting of N,N-dimethylacetamide and N,N-dimethylformamide; and
the tri(oxybenzene-amine) crosslinker is selected from the group consisting of tris[(4-aminophenoxy)phenyl]borate, tris[(2-chloro-4-aminophenoxy)phenyl]borate, tris [(2-chloro-4-aminophenoxy)phenyl]borate, tris[(2-fluoro-4-aminophenoxy)phenyl]borate, tris[(2-methyl-4-aminophenoxy)phenyl]borate, tris[(2-trifluoromethyl-4-aminophenoxy)phenyl]borate, tris [(2-chloro-5-aminophenoxy)phenyl]borate, tris[(2-fluoro-5-aminophenoxy)phenyl]borate, tris[(2-trifluoromethyl-5-aminophenoxy)phenyl]borate.

15. The method of claim 12 wherein the aromatic diamine is 1,3-bis(3-aminophenoxy)benzene;
the dianhydride monomer is selected from the group consisting of 2,2-bis(phthalic anhydride)-1,1,1,3,3,3-hexafluoroisopropane, 4,4'-oxydi(phthalic anhydride), 3,3',4,4'-diphenylsulfone tetracarboxylic dianhydride, 3,3',4,4'-benzophenone tetracarboxylic dianhydride, 4,4'-(2,2,2-trifluoro-1-phenylethylidene)diphthalic anhydride, 2,2-bis[4-(3,4-dicarboxyphenoxy)phenyl] propane dianhydride, 4,4'-(p-phenylenedioxy)diphthalic anhydride, and 4,4'-(m-phenylenedioxy)diphthalic anhydride;
the polar solvent is selected from the group consisting of N,N-dimethylacetamide and N,N-dimethylformamide; and
the tri(oxybenzene-amine) crosslinker is selected from the group consisting of tris[(4-aminophenoxy)phenyl]phosphine oxide, tris[(4-aminophenoxy)phenyl]phosphine oxide, tris[(2-fluoro-4-aminophenoxy)phenyl]phosphine oxide, tris[(2-methyl-4-aminophenoxy)phenyl] phosphine oxide, tris[(2-trifluoromethyl-4-aminophenoxy)phenyl]phosphine oxide, tris[(2-chloro-5-aminophenoxy)phenyl]phosphine oxide, tris[(2-trifluoromethyl-5-aminophenoxy)phenyl]phosphine oxide, tris[(2-methyl-5-aminophenoxy)phenyl]phosphine oxide, tris[(2-fluoro-5-aminophenoxy)phenyl] phosphine oxide.

16. The method of claim 15 wherein the aromatic diamine is 1,3-bis(3-aminophenoxy)benzene, the dianhydride monomer is 2,2-bis(phthalic anhydride)-1,1,1,3,3,3-hexafluoroisopropane, the polar solvent is N,N-dimethylacetamide, and the tri(oxybenzene-amine) crosslinker is tris[(4-aminophenoxy)phenyl]phosphine oxide.

* * * * *